United States Patent [19]

Serkes et al.

[11] Patent Number: 4,824,787

[45] Date of Patent: Apr. 25, 1989

[54] ROLLER BOTTLE FOR TISSUE CULTURE GROWTH

[75] Inventors: Jonathan M. Serkes, Oak View; William L. Foschaar, Camarillo, both of Calif.

[73] Assignee: In Vitro Scientific Products, Inc., Ventura, Calif.

[21] Appl. No.: 130,740

[22] Filed: Feb. 16, 1988

[51] Int. Cl.⁴ .......................... C12M 3/00; C12M 3/04
[52] U.S. Cl. ..................... 435/285; 215/1 C; 215/1 R; 220/72; 422/102; 435/284; 435/296; 435/312
[58] Field of Search ................. 435/240.23, 284–286, 435/296, 310, 312; 422/99, 102; 215/1 C, 1 R; 220/72

[56] References Cited

U.S. PATENT DOCUMENTS

| 4,024,975 | 5/1977 | Uhlig | 215/1 C |
| 4,178,976 | 12/1979 | Weiler et al. | 215/1 C |
| 4,717,668 | 1/1988 | Keilman et al. | 435/286 |

Primary Examiner—Michael S. Marcus
Assistant Examiner—Timothy M. McMahon
Attorney, Agent, or Firm—Marvin E. Jacobs

[57] ABSTRACT

A roller bottle for cell growth contains a wall formed of a plurality of corrugations, preferably symmetrical and perpendicular to the axis of the bottle, and at least one drain channel formed by at least one and preferably two opposed flat axial, uncorrugated panels provided along the outer edge of the corrugations. The corrugations are discontinuous along the inside surface of the panel to form a drainage channel. The surface area of the bottle is 110 to 500% larger than an uncorrugated bottle having the same exterior dimensions.

13 Claims, 2 Drawing Sheets

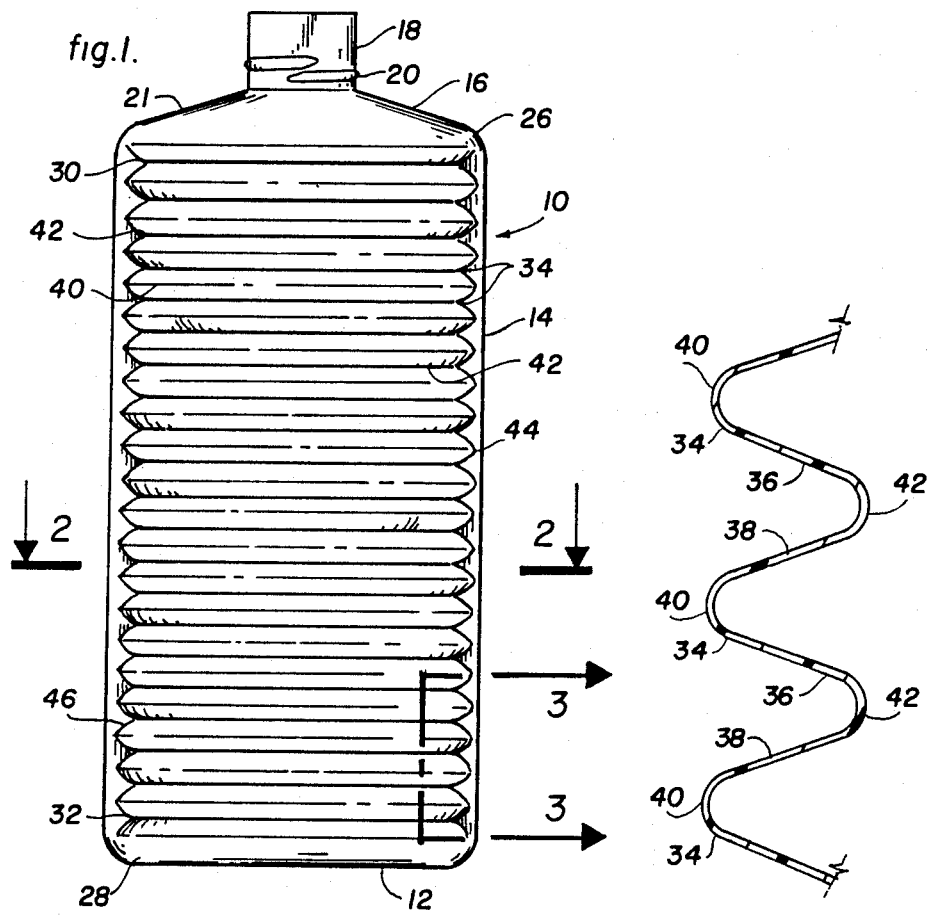
fig.1.
fig.3.
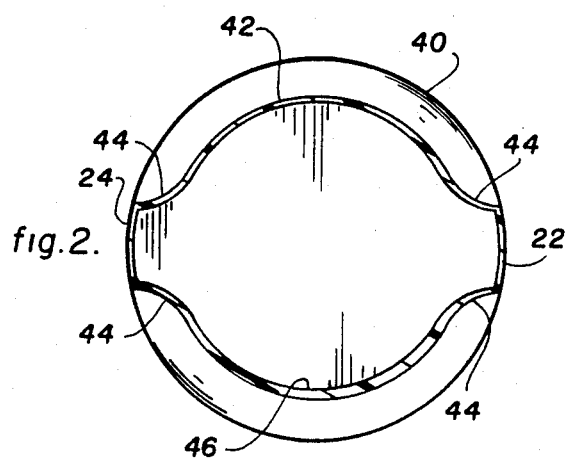
fig.2.

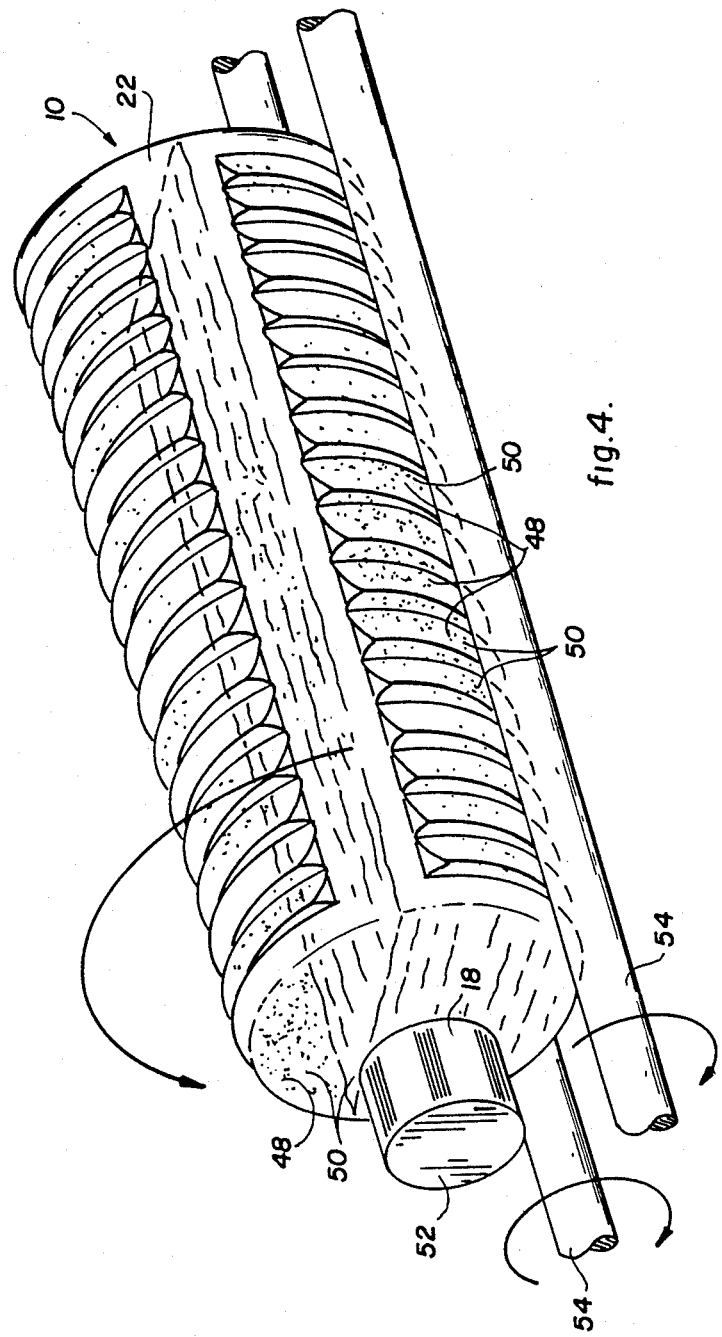

ROLLER BOTTLE FOR TISSUE CULTURE GROWTH

TECHNICAL FIELD

The invention relates to biotechnology apparatus and, more particularly, this invention relates to a roller bottle for tissue culture growth.

Genetic engineering is progressing to a commercially profitable stage with the recent government approval of several genetically engineered products--especially pharmaceutical products expressed from animal cells, such as interferon, human growth hormone, insulin, tissue plasminogen activator (TPA) and erythropoiten (EPO). It is estimated that 20% of the $60 billion of pharmaceuticals presently produced by chemical methods could be produced by simpler and more economical biotechnology methods. The next stage of the industry's growth will involve large scale cell culture.

The early protein products produced by genetic engineering were produced in single cell bacterial or yeast cells. Bacterial and viruses are simple biological cells that are not capable of producing the more complex molecules and combinations of molecules. TPA and EPO are glycoproteins. The simple proteins produced by bacteria or yeast cells must be glycosylated in a separate step. Furthermore, bacterial cells do not usually secrete the desired protein into the surrounding medium. They must be chemically or mechanically fragmented in order to harvest the desired protein.

Mammalian cells can produce sugar modified proteins and more importantly, they often secrete the desired glycoprotein product into the medium for easy collection. However, mammalian cells are very fragile. They contain a delicate membrane that is easily ruptured or damaged by abrasion from the surface of a bioreactor or by the propellers of a conventional bacterial fermenter. Once the membrane is ruptured, the cell dies.

Another difficulty with mammalian cells is that they grow slowly. Unlike bacteria which divides 2 to 3 times an hour, mammalian cells divide only every 18 to 48 hours. Also a mammalian cell is not a self-sufficient organism. It is part of a much larger organism and demands a steady stream of nutrients, hormones and other compounds to survive and grow.

Most mammalian cells must be attached to a support or substrate similar to their condition in a living organism. Many biotechnology processes culture mammalian cells while anchored to the surface of a roller bottle. In order to increase the surface area for attachment in some culture processes, the cells have been attached to inert beads, embedded in a gel or attached to the surface of a hollow fiber. These systems are complex and expensive and can result in stagnant regions which do not receive adequate nutrients and/or build-up excessive waste products.

Roller bottles have been used extensively to culture animal cells while attached to the inside surface of the bottles. There is a large number of roller bottle reactor systems in place within biotechnology and animal vaccine companies. These reactor systems are still suitable for short-term batch runs. However, the economy and efficiency could be greatly increased if the amount of cells processed per bottle could be increased.

| List of Prior Art | |
|---|---|
| PATENT NO. | PATENTEE |
| 3,249,504 | L. R. Cappel et al |
| 3,589,983 | Holderith et al |
| 3,893,887 | Smith et al |
| 4,176,756 | Gellman |
| 4,238,568 | Robert W. Lynn |
| 4,283,495 | Robert W. Lynn |
| 4,317,886 | Johnson et al |
| 4,337,104 | Robert W. Lynn |
| D 285,725 | Larry A. Franchere |
| 4,657,867 | Guhl et al |

DESCRIPTION OF THE PRIOR ART

Johnson et al discloses providing an extended growth surface by means of a plurality of concentric rings in the form of cylindrical inserts parallel to the axis of the bottle. Clips are required to maintain separation between the cylindrical inserts. The embodiment of FIG. 5 indicates the inserts can have a corrugated surface. The corrugations would be parallel to the axis of the bottle. The Johnson et al bottle is manufactured in several separate parts which are then assembled and adhered together to form a sealed enclosure. The bottle is too expensive and has not provided the intended benefits. This bottle is not commercially available.

The Lynn patents require exterior circumferential serrations. Gelmann relates to a stopper lock for a culture bottle. The Franchere patent relates to a rectangular tissue container. Holderith discloses a tray insert for a bottle. Smith et al discloses a method for programmed control of a tilting apparatus for roller bottles. Cappel deals with a two container system, one for the stable liquid ingredients and one for the dried, labile ingredients. Guhl et al discloses a multicell tissue culture apparatus.

Due to the constraints of the roller apparatus, the roller bottles must have a specified circumference and length. Therefore, it was accepted that the external configuration could not be changed. Johnson added the cylindrical inserts to the roller bottle since he believed that was the only way to the increase cell attachment surface of the bottle.

STATEMENT OF THE INVENTION

An improved roller bottle with greatly increased surface area for tissue growth is provided in accordance with the invention. The roller bottle is more easily manufactured in a single step process as a unitary piece and is able to increase surface area for cell attachment without changing the external dimensions or essential configuration of the bottle.

The roller bottle of the invention contains cell growth attachment surfaces that are attached to and extend inwardly a distance from the inside surface of the bottle. In a first configuration, a plurality of baffles were attached to the wall of the bottle. These baffles significantly increased surface area of the bottle. However, it was found that some of the cells detached from the baffles during roller operation. It was found that the cells would more reliably maintain attachment to a surface that slanted, suitably by an angle of from 10° to 80° with the wall surface.

A preferred configuration for the slanted surface is provided by means of accordion-like pleats which form the side wall of the bottle. The two slanted surfaces connect to form an inner corrugation. Adjacent corrugations intersect to form a plurality of outer bands which ride on the rollers. The bottles are periodically drained to remove waste product, harvest expressed product or to harvest cells. The corrugated, pleated surfaces act as channels for the liquid nutrient during rolling of the bottle. However, during drainage they act as dams preventing easy drainage.

Another feature of the roller bottle of the invention is the provision of at least 1, preferably at least 2, drain channels in the form of an unpleated segment of the sidewall, parallel to the axis of the bottle running as a band from near the top to near the bottom of the bottle. The drain channel is formed along the outer edges of the pleats along the outer circumference of the bands so that the bottle rolls smoothly on the roller cylinders of the roller apparatus. Another benefit of the drain channels is the support they provide to the bottle. The corrugated pleats tend to be weak and can cause accordion-like stretching or compression of the bottle when handled or bending of the bottle under the weight of the liquid nutrient medium. Repeated flexing of the pleats can cause fatigue and rupture, especially during the long periods of use during the cell culturing batch process. However, the drain channels act as beams preventing bending, extension or compression of the corrugated pleats.

These and many other features and attendant advantages of the invention will become apparent as the invention becomes better understood by reference to the following detailed description when considered in conjunction with the accompanying drawings.

BRIEF DESCRIPTION OF THE DRAWINGS

FIG. 1 is a front view in elevation of an embodiment of the roller bottle of the invention;

FIG. 2 is an enlarged, detailed view in section taken along line 2—2 of FIG. 1;

FIG. 3 is a cross-sectional view taken along line 3—3 of FIG. 1, and

FIG. 4 is a perspective view of the roller bottle shown on a set of schematic rollers.

DETAILED DESCRIPTION OF THE INVENTION

Referring now to FIGS. 1-3, the roller bottle 10 is a generally cylindrical member formed of a bottom 12, a corrugated, pleated mid-section 14 and a top section 16 having a neck 18 containing a spiral thread 20 for attachment of a cap, not shown. The pleated mid-section 14 contains at least one drain channel 22, preferably at least two drain channels 22, 24 disposed in opposed relation. The juncture 26 of the top and juncture 28 of the bottom with the mid-section are preferably rounded to reduce stress and fracture surfaces. Though expanses of solid wall could be provided between the bottom 12 or top 16 and the top pleat 30 or the bottom pleat 32, these wall sections are usually avoided in order to maximize the number of pleats and thus maximize the surface area.

Though some surface area of the wall is removed by the drainage channel, the surface area is increased by at least 110% over an unpleated bottle of the same exterior dimensions. The typical standard bottle is a disposable plastic bottle having a 850cm² surface area. The maximum surface area increase will usually be no more than 500% to maintain volume for the cell culture medium and to maintain structural integrity of the bottle. The optimum design appears to be about 200 to 250% increase in surface area. The number of pleats or corrugations depends on the amplitude of the corrugations, the pitch of the corrugations and the height and volume of the bottle. Generally, a conventional 2¼ liter roller bottle will contain 10 to 50 corrugations, usually about 20 to 40 corrugations. The width of the panels forming, the drain channel is not critical except that the panels represent a loss of increased surface area. The channels are preferably maintained between 5 to 20% of the circumference of the bottle.

Referring now to FIG. 3, the pitch or angle of the corrugations 34 is designed so that the liquid culture medium drains toward the drain channels 22, 24. The corrugations in a commercial mineral water bottle slant downwardly so that the mineral water pours readily out of the top. The corrugations 34 in the roller bottle of the invention are preferably symmetrical with the upper surface 36 and the lower surface 38 having an equal length and pitch with respect to a plane normal to the axis of the bottle through the inner juncture 40 of the two surfaces 36, 38. The juncture 40 is preferably rounded since it is easier for the cells to stick to a rounded rather than a sharp, pointed surface and the rounded juncture is easier to form by casting or molding. A rounded surface is also stronger and less subject to cracking on flexing.

The radius of the curved edge of the juncture 40 is at least 0.010 inches preferably from 0.05 to 0.10 inches. The amplitude can be from 0.2 to 0.5 inches, generally about 0.3 to 0.4 inches. This provides a spacing of about 0.1 to 0.5 inches between corrugations 34.

The bottle is manufactured from a biocompatible, resin material that can be subject to radiation for sterilization and surface treatment which provides a wettable surface for attachment of the cells. The resin material should also be able to withstand long-term rolling in the environment of the roller apparatus. The roller bottle of the invention can be manufactured in a single stage by various molding procedures.

The wall of the bottle has a sufficient thickness to form a bottle of adequate strength when filled with cell culturing medium. Generally, the film thickness will be from 1 to 60 thousands for a 2.25 liter roller bottle. The resin must be able to readily flow to form the small radius corrugations. The resin must not have any extractibles in order to be approved by the FDA for use in biotechnology processes. Transparent, thermoplastic resins such as polyethyleneglycol-polyesters, have been found suitable for forming the roller bottle of the invention by extrusion blow or injection blow molding techniques.

Referring again to FIGS. 1 and 2, the outer circumferential surface for rolling the bottle 10 is formed by the two panels 22, 24 of the drains and the rims 42 forming the outer junctures of the walls 36, 38 of the corrugations 34. The inner terminus of each corrugation 34 adjacent the drain channels 24, 26 is faced with a triangular wall 44 which slopes toward the channel 22, 24 acting as a smooth ramp for channelling the liquid or suspension into the interior channels 46 inside each corrugation 34.

The top 16 has a sloping surface 21 to aid in draining the culture medium out of the bottle 10. The bottom 12 may be flat or can have a concave cavity for receiving the neck of an adjacent bottle for closer nesting on the roller apparatus.

The interior surface of a 2.25 liter roller bottle having a height of about 10.5 inches and a width of about 5 inches containing 21 corrugations with an amplitude of 0.312 inches, a radius of 0.062 inches and a spacing of 0.403 inches was calculated to about 1725 cm². This is about twice the surface area of the standard 2.25 liter bottle of the same exterior dimensions.

Referring now to FIG. 4, the roller bottle 10 of the invention is first treated tb prepare the surface for adhesion of cells, and is sterilized by radiation or other technique. The bottle is then filled with cells which form a layer 48 on the inside surface of the bottle. Liquid nutrient culture medium 50 is then added to the bottle and a liquid tight or breathable cap 52 is placed on the neck 18 of the bottle. The bottle is placed on horizontal rollers 54 and is rolled during processing. At an intermediate stage or at the conclusion of processing, the roller bottle is positioned with either drain channel 22, 24 in a downward position. The cap 52 is removed and the bottle 10 is tilted to drain the medium 50 from the bottle.

The roller bottles of the invention have been tested in a plurality of runs of tissue culture growth and are found to provide almost double the yield of product compared to bottles of the same exterior dimensions. The bottles are readily fabricated in one step and are found to provide good clarity and transparency even in the corrugated mid-section. The roller bottles will find use in production of vaccines and, culturing of adhering animal or human cells.

It is to be realized that only preferred embodiments of the invention have been described and that numerous substitutions, modifications and alterations are permissible without departing from the spirit and scope of the invention as defined in the following claims.

I claim:

1. A roller bottle for tissue culture growth comprising in combination:
    a substantially cyclindrical wall section having a central axis and containing a pleated segment having an upper edge and a lower edge;
    the pleated segment including at least one unpleated panel for forming a drain channel for emptying the contents of the bottle and a plurality of pleats disposed crosswise to the axis of the bottle, each of the pleats containing an outer rim disposed in a common cylindrical plane and forming a trough on the inside surface of the segment;
    each of the panels being connected to said troughs, being disposed no nearer to said central axis than said common cylindrical plane and extending substantially from the upper edge to the lower edge of the cylindrical segment;
    said roller bottle having an inner surface area at least 110% larger than the surface area of a roller bottle having an unpleated cylindrical segment having the same external diameter;
    a top section of the bottle having a neck connected to the cylindrical wall section; and
    a bottom section of the bottle connected to the cylindrical wall section.

2. A roller bottle according to claim 1 in which the inner surface area of the bottle is from 110% to 500% the inner surface area of a roller bottle having an unpleated cylindrical segment having the same external diameter.

3. A roller bottle according to claim 1 in which the wall contains from 1-4 of said panels.

4. A roller bottle according to claim 3 formed of a clear, sterilizable and wettable synthetic resin.

5. A roller bottle according to claim 3 in which the panels from no more that 20% of the circumference of the wall section.

6. A roller bottle according to claim 5 in which two opposed panels are provided in pleated segment.

7. A roller bottle according to claim 3 further including internal triangular wall closures extending from the inner edge of each pleat to the inner edge of the panel.

8. A roller bottle according to claim 7 in which the wall closures are sloped.

9. A roller bottle according to claim 3 in which the outer surface of the top section has a convex, sloped configuration.

10. A roller bottle according to claim 9 in which the ourter surface of the neck contains a spiral thread.

11. A roller bottle according to claim 3 in which the pleated segment contains from 10 to 50 pleats.

12. A roller bottle according to claim 11 in which the pleats extend substantially along the entire length of said cylindrical wall section.

13. A roller bottle according to claim 11 in which the inner edges of the trough and the outer edges of the rims of the pleats are rounded.

* * * * *

UNITED STATES PATENT AND TRADEMARK OFFICE
CERTIFICATE OF CORRECTION

PATENT NO. : 4,824,787
DATED : April 25, 1989
INVENTOR(S) : Jonathan M. Serkes, William L. Foschaar It is certified that error appears in the above-identified patent and that said Letters Patent is hereby corrected as shown below:

Title Page, Item [22] change "Feb. 16, 1988" to --Dec. 9, 1987--.

Signed and Sealed this

Twelfth Day of December, 1989

*Attest:*

JEFFREY M. SAMUELS

*Attesting Officer*     *Acting Commissioner of Patents and Trademarks*

REEXAMINATION CERTIFICATE (1307th)
United States Patent [19]
Serkes et al.

[11] B1 4,824,787
[45] Certificate Issued  Jun. 12, 1990

[54] ROLLER BOTTLE FOR TISSUE CULTURE GROWTH

[75] Inventors: Jonathan M. Serkes, Oak View; William L. Foschaar, Camarillo, both of Calif.

[73] Assignee: In Vitro Scientific Products, Inc., Oakview, Calif.

Reexamination Request:
No. 90/001,818, Aug. 7, 1989

Reexamination Certificate for:
Patent No.: 4,824,787
Issued: Apr. 25, 1989
Appl. No.: 130,740
Filed: Feb. 16, 1988

Certificate of Correction issued Dec. 12, 1989.

[51] Int. Cl.⁵ .................... C12M 3/00; C12M 3/04
[52] U.S. Cl. ........................... 435/285; 215/1 C; 215/1 R; 220/72; 422/102; 435/284; 435/296; 435/312
[58] Field of Search ............... 435/240.23, 284, 285, 435/286, 296, 310, 312; 422/99, 102; 215/1 C, 1 R; 220/72

[56] References Cited
U.S. PATENT DOCUMENTS
4,317,886  3/1982  Johnson et al. .

FOREIGN PATENT DOCUMENTS
1191951  10/1959  France .

OTHER PUBLICATIONS
Plasma Science, Technical Notes, 8/88, No. 5.
Ryan, John A., "Identifying and Correcting Common Cell Culture Growth and Attachment Problems," ABL Cell Culture, Jan. 1989.
Ramsey et al., "Surface Treatments and Cell Attachment," In Vitro, vol. 20, No. 10, Oct. 1984.

Primary Examiner—Robert J. Warden

[57] ABSTRACT

A roller bottle for cell growth contains a wall formed of a plurality of corrugations, preferably symmetrical and perpendicular to the axis of the bottle, and at least one drain channel formed by at least one and preferably two opposed flat axial, uncorrugated panels provided along the outer edge of the corrugations. The corrugations are discontinuous along the inside surface of the panel to form a drainage channel. The surface area of the bottle is 110 to 500% larger than an uncorrugated bottle having the same exterior dimensions.

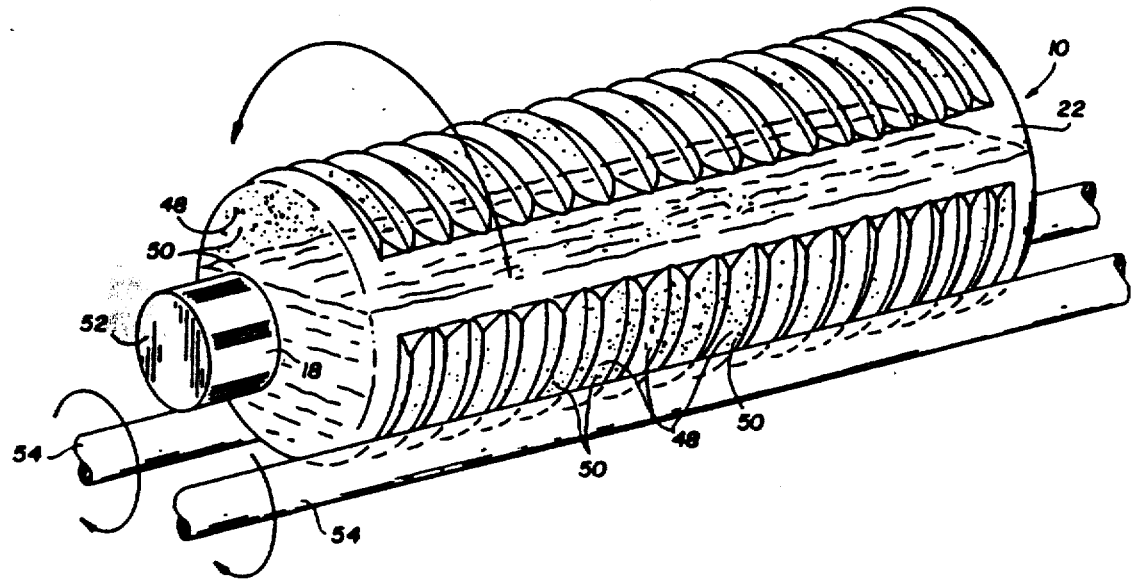

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, lines 60 to Column 4, line 11.

Though some surface area of the wall is removed by the drainage channel, the surface area is increased by at least 110% [over], *preferably at least 160% the surface area of* an unpleated bottle of the same exterior dimensions. The typical standard bottle is a disposable plastic bottle having a 850 cm² surface area. The maximum surface area increase will usually be no more than 500% to maintain volume for the cell culture medium and to maintain structural integrity of the bottle. The optimum design appears to be about 200 to 250% [increase in] *the surface area of an unpleated bottle of the same exterior dimensions*. The number of pleats or corrugations depends on the amplitude of the corrugations, the pitch of the corrugations and the height and volume of the bottle. Generally, a conventional 2¼ liter roller bottle will contain 10 to 50 corrugations, usually about 20 to 40 corrugations. The width of the panels forming, the drain channel is not critical except that the panels represent a loss of increased surface area. The [channels] *panels* are preferably maintained between 5 to 20%, *preferably at least 13% of the circumference of the bottle with each panel being at least 5% preferably at least 6.5% of the circumference of the bottle.*

AS A RESULT OF REEXAMINATION, IT HAS BEEN DETERMINED THAT:

Claim 1 is determined to be patentable as amended.

Claims 2–13, dependent on an amended claim, are determined to be patentable.

New Claims 14–28 are added and determined to be patentable.

1. A roller bottle for tissue culture growth comprising in combination:
   a substantially cylindrical wall section having a central axis and containing a pleated segment having an upper edge and a lower edge;
   the pleated segment including at least one unpleated panel for forming a drain channel for emptying the contents of the bottle, *said panel forming at least 5% of the circumference of the wall section*, and a plurality of pleats disposed crosswise to the axis of the bottle, each of the pleats containing an outer rim disposed in a common cylindrical plane and forming a trough on the inside surface of the segment;
   each of the panels being connected to said troughs, being disposed no nearer to said central axis than said common cylindrical plane and extending substantially from the upper edge to the lower edge of the cylindrical segment;
   said roller bottle having an inner surface area at least 110% [larger than] the surface area of a roller bottle having an unpleated cylindrical segment having the same external diameter;
   a top section of the bottle having a neck connected to the cylindrical wall section; and
   a bottom section of the bottle connected to the cylindrical wall section.

*14. A roller bottle according to claim 2 in which the inner surface area of the bottle is at least about 160% the surface area of a roller bottle having an unpleated, cylindrical segment of the same external diameter.*

*15. A roller bottle according to claim 11 in which the pleated segment contains from about 20 to about 40 pleats and the surface area is from at least 200% to 250% the surface area of a roller bottle having an unpleated cylindrical segment of the same external diameter.*

*16. A roller bottle according to claim 5 in which the panels form from about 5% to about 20% of the circumference of the cylindrical wall section.*

*17. A roller bottle according to claim 16 in which the panels form at least about 13% of the circumference of the cylindrical wall section.*

*18. A roller bottle according to claim 16 in which each panel forms at least about 6.5% of the circumference of the cylindrical wall section.*

*19. A roller bottle according to claim 1 in which the cylindrical wall section includes a first unpleated cylindrical segment connecting the upper edge of the pleated segment to the top section of the bottle and a second, unpleated, cylindrical segment connecting the lower edge of the pleated segment to the bottom section of the bottle.*

*20. A roller bottle according to claim 4 containing a layer of cells adhered to the inside surface of the bottle.*

*21. A roller bottle according to claim 20 in which the inside surface of the bottle has been radiation treated to provide a wettable and sterilized surface for attachment and growth of cells.*

*22. A roller bottle according to claim 10 in which a liquid tight cap is received on the spiral thread.*

*23. A roller bottle according to claim 1 having a volumetric capacity of about 2.25 liters and a surface area of about 1725 cm².*

*24. A roller bottle for tissue culture growth comprising in combination:*
   *a substantially cylindrical wall section having a central axis and containing a pleated segment, said wall section having an upper edge and a lower edge;*
   *the wall of the pleated segment containing from 10–50 transverse pleats disposed crosswise to the axis of the bottle, each of the pleats containing an outer rim disposed in a common cylindrical plane and forming a trough on the inside surface of the segment and at least one flat, unpleated, axial panel for forming a drain channel for emptying the contents of the bottle, said flat panel forming at least about 6.5% of the circumference of the cylindrical wall-section;*
   *said roller bottle having an inner surface at least about 160% the surface area of a roller bottle having an unpleated cylindrical segment having the same external diameter;*
   *a top section of the bottle having a neck connected to the cylindrical wall section; and*
   *a bottom section of the bottle connected to the cylindrical wall section.*

25. A roller bottle according to claim 24 in which the segment contains from 20-40 transverse pleats, at least 2 flat, unpleated axial panels and the surface is from about 200 percent to about 250 percent the surface area of a roller bottle having an unpleated cylindrical segment of the same external diameter.

26. A roller bottle according to claim 25 formed of a transparent, thermoplastic resin.

27. A roller bottle for tissue culture growth comprising in combination:
   a substantially cylindrical wall section having a central axis and containing a pleated segment having an upper edge and a lower edge;
   the pleated segment including at least one unpleated panel for forming a drain channel for emptying the contents of the bottle and a plurality of pleats disposed crosswise to the axis of the bottle, each of the pleats containing an outer rim disposed in a common cylindrical plane and forming a trough on the inside surface of the segment;
   each of the panels being connected to said troughs, being disposed no nearer to said central axis than said common cylindrical plane and extending substantially from the upper edge to the lower edge of the cylindrical segment;
   said roller bottle having an inner surface area at least 110% the surface area of a roller bottle having an unpleated cylindrical segment having the same external diameter;
   a top section of the bottle having a neck connected to the cylindrical wall section;
   a bottom section of the bottle connected to the cylindrical wall section; and
   the bottle being formed of a synthetic resin and the inside surface of the bottle being treated to be wettable for attachment and growth of cells.

28. A roller bottle for tissue culture growth formed of a clear, sterilizable and wettable synthetic resin comprising in combination:
   a substantially cylindrical wall section having a central axis and containing a pleated segment having an upper edge and a lower edge;
   the pleated segment including from 1 to 4 unpleated panels for forming a drain channel for emptying the contents of the bottle and a plurality of pleats disposed crosswise to the axis of the bottle, each of the pleats containing an outer rim disposed in a common cylindrical plane and forming a trough on the inside surface of the segment;
   each of the panels being connected to said troughs, being disposed no nearer to said central axis than said common cylindrical plane and extending substantially from the upper edge to the lower edge of the cylindrical segment;
   said roller bottle having an inner surface area at least 110% larger than the surface area of a roller bottle having an unpleated cylindrical segment having the same external diameter;
   a top section of the bottle connected to the cylindrical wall section; and
   a bottom section of the bottle connected to the cylindrical wall section.

* * * * *